United States Patent [19]

Berthold

[11] 4,235,919
[45] Nov. 25, 1980

[54] 1-(INDOL-4-YLOXY)-3-(2-SUBSTITUTED AMINO)-2-PROPANOLS AND PHARMACEUTICAL USE THEREOF

[75] Inventor: Richard Berthold, Bottmingen, Switzerland

[73] Assignee: Sandoz Ltd., Basel, Switzerland

[21] Appl. No.: 925,196

[22] Filed: Jul. 17, 1978

[30] Foreign Application Priority Data

| Jul. 21, 1977 | [CH] | Switzerland | 9065/77 |
| Jul. 21, 1977 | [CH] | Switzerland | 9069/77 |
| Jul. 21, 1977 | [CH] | Switzerland | 9070/77 |
| Jul. 21, 1977 | [CH] | Switzerland | 9072/77 |
| Jul. 21, 1977 | [CH] | Switzerland | 9073/77 |
| Jul. 21, 1977 | [CH] | Switzerland | 9077/77 |

[51] Int. Cl.³ .................. A61K 31/40; C07D 209/18; C07D 209/00
[52] U.S. Cl. .................. 424/274; 260/326.14 R
[58] Field of Search ................ 260/326.14 R; 424/274

[56] References Cited

U.S. PATENT DOCUMENTS

| 3,340,266 | 9/1967  | Howe et al.     | 260/288       |
| 3,432,545 | 3/1969  | Howe et al.     | 260/501.17    |
| 3,696,120 | 10/1972 | Troxler         | 260/326.14 R  |
| 3,696,121 | 10/1972 | Troxler         | 260/326.15    |
| 3,699,123 | 10/1972 | Seeman et al.   | 260/326.14 R  |
| 3,705,907 | 12/1972 | Troxler         | 260/326.14 R  |
| 3,751,429 | 8/1973  | Seeman et al.   | 260/326.14 R  |

FOREIGN PATENT DOCUMENTS

| 527188  | 10/1972 | Belgium        |
| 1129072 | 10/1968 | United Kingdom |
| 1269776 | 4/1972  | United Kingdom |
| 1493006 | 11/1977 | United Kingdom |

OTHER PUBLICATIONS

Cram et al., Organic Chem. 2nd Ed. McGraw Hill N. Y. (1964), pp. 255 & 256.
Suvorov et al., Chem. Abst. 80, 70637p (1974).

*Primary Examiner*—Donald G. Daus
*Assistant Examiner*—D. B. Springer
*Attorney, Agent, or Firm*—Gerald D. Sharkin; Robert S. Honor

[57] ABSTRACT

The compounds of formula I

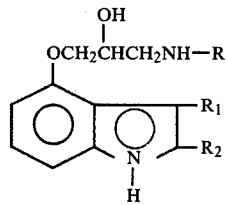

wherein
R is a group

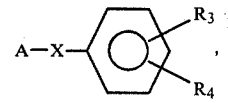

wherein
A is alkylene of 2 to 5 carbon atoms,
X is a bond, oxygen or sulfur,
$R_3$ is hydrogen, hydroxy, alkoxy of 1 to 4 carbon atoms, halogen of atomic member of from 9 to 35, cyano, carbamoyl or a group $NHCOR_d$, wherein $R_d$ is alkyl of 1 to 4 carbon atoms, and
$R_4$ is hydrogen and, when $R_3$ is alkoxy of 1 to 4 carbon atoms, $R_4$ additionally may be alkoxy of 1 to 4 carbon atoms or, when $R_3$ is halogen of atomic number of from 9 to 35, $R_4$ additionally may be halogen of atomic number of from 9 to 35 either
(i) $R_1$ is hydrogen or methyl and
   $R_2$ is cyano, $CONR_aR_b$, $COOR_c$ or $CH_2OR_e$, wherein $R_a$, $R_b$, $R_c$ and $R_e$ independently are hydrogen or alkyl of 1 to 4 carbon atoms,
or
(ii) either $R_1$ is methyl and $R_2$ is halogen of atomic number of from 17 to 35
or $R_1$ is halogen of atomic number of from 17 to 35 and $R_2$ is hydrogen or methyl,
with the provisos that
(a) X is separated from the nitrogen atom of the 3-amino-2-hydroxypropoxy chain by at least 2 carbon atoms,
(b) when X is a bond, $R_3$ is other than hydrogen and
(c) when $R_2$ is cyano, R additionally may be alkyl of 3 to 7 carbon atoms,
are useful as α- and β-adrenoceptor blocking, antiarrhythmic and antihypertensive agents and as inhibitors of metabolic effects of emotional stress.

38 Claims, No Drawings

1-(INDOL-4-YLOXY)-3-(2-SUBSTITUTED AMINO)-2-PROPANOLS AND PHARMACEUTICAL USE THEREOF

The present invention relates to 1-(indol-4-yloxy)-3-amino-2-propanol derivatives.

In accordance with the invention there are provided compounds of formula I

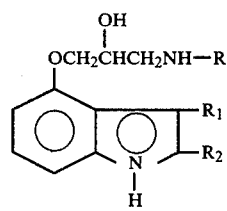

wherein
R is a group

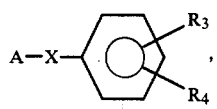

wherein
A is alkylene of 2 to 5 carbon atoms,
X is a bond, oxygen or sulfur,
$R_3$ is hydrogen, hydroxy, alkoxy of 1 to 4 carbon atoms, halogen of atomic member of from 9 to 35, cyano, carbamoyl or a group $NHCOR_d$, wherein $R_d$ is alkyl of 1 to 4 carbon atoms, and
$R_4$ is hydrogen and, when $R_3$ is alkoxy of 1 to 4 carbon atoms, $R_4$ additionally may be alkoxy of 1 to 4 carbon atoms or, when $R_3$ is halogen of atomic number of from 9 to 35, $R_4$ additionally may be halogen of atomic number of from 9 to 35
either
(i) $R_1$ is hydrogen or methyl and
$R_2$ is cyano, $CONR_aR_b$, $COOR_c$ or $CH_2OR_e$, wherein $R_a$, $R_b$, $R_c$ and $R_e$ independently are hydrogen or alkyl of 1 to 4 carbon atoms, or
(ii) either $R_1$ is methyl and $R_2$ is halogen of atomic number of from 17 to 35
or $R_1$ is halogen of atomic number of from 17 to 35 and $R_2$ is hydrogen or methyl,
with the provisos that
(a) X is separated from the nitrogen atom of the 3-amino-2-hydroxypropoxy chain by at least 2 carbon atoms,
(b) when X is a bond, $R_3$ is other than hydrogen and
(c) when $R_2$ is cyano, R additionally may be alkyl of 3 to 7 carbon atoms.
R preferably is a group

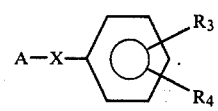

X preferably is a bond or oxygen. $R_3$ preferably is hydrogen, hydroxy or alkoxy. $R_4$ preferably is hydrogen or alkoxy. $R_1$ preferably is hydrogen or halogen. $R_2$ preferably is methyl, cyano or $CONR_aR_b$. $R_a$, $R_b$ and $R_e$ preferably are hydrogen. $R_c$ preferably is alkyl.

Alkyl (except as indicated hereunder for R and $R_c$) and/or alkoxy preferably are of 1 or 2, especially of 1 carbon atom. When R is alkyl, it preferably is of 3 to 5 carbon atoms and preferably is branched, especially in the position α to the nitrogen atom to which it is bound. Interesting alkyl groups R are e.g. isopropyl, tert-butyl and 3-pentyl, especially tert-butyl. When $R_c$ is alkyl, it preferably is of 1 to 3 carbon atoms; when it is of more than 2 carbon atoms, it preferably is branched, as e.g. in isopropyl.

Halogen preferably is bromine of chlorine, especially chlorine. A preferably is branched alkylene, especially in the position α to the nitrogen atom to which it is bound, e.g. the group

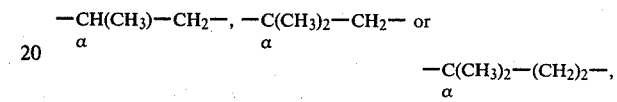

or it is ethylene.

When $R_3$ and $R_4$ are hydrogen, X preferably is oxygen. When $R_3$ is not hydrogen, X preferably is a bond. When $R_3$ is not hydrogen, it preferably is in the para position. When $R_4$ is not hydrogen, it preferably is in the meta position. When $R_4$ is alkoxy or halogen, it preferably is identical to $R_3$.

A group of compounds of formula I are the compounds of formula Ix

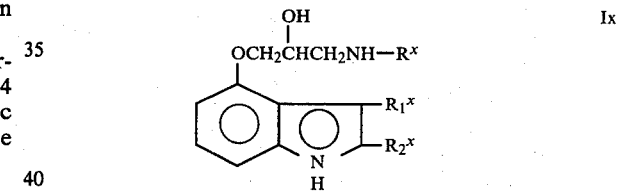

wherein
$R^x$ is a group

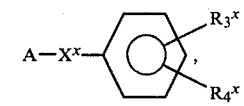

wherein A is as defined above,
either
(i) $X^x$ is oxygen or sulfur and $R_1^x$ to $R_4^x$ have the significances indicated above for $R_1$ to $R_4$
or
(ii) $X^x$ is a bond and
either
(j) $R_3^x$ is alkoxy of 1 to 4 carbon atoms or halogen of atomic number of from 9 to 35,
$R_4^x$ is hydrogen and, when $R_3^x$ is alkoxy of 1 to 4 carbon atoms, $R_4^x$ additionally may be alkoxy of 1 to 4 carbon atoms or, when $R_3^x$ is halogen of atomic number of from 9 to 35, $R_4^x$ additionally may be halogen of atomic number of from 9 to 35,
$R_1^x$ is hydrogen of methyl and
$R_2^x$ is $CONR_aR_b$, wherein $R_a$ and $R_b$ are as defined above,
or (jj) $R_3^x$ is hydroxy, cyano, carbamoyl or $NHCOR_d$, wherein $R_d$ is as defined above, $R_4^x$ is hydrogen and $R_1^x$ and $R_2^x$ have the significances indicated above for $R_1$ and $R_2$, with the proviso, that $X^x$ is separated by at least 2 carbon atoms from the nitrogen atom of the 3-amino-2-hydroxypropoxy chain.

A group of compounds of formula Ix are the compounds of formula Ix'

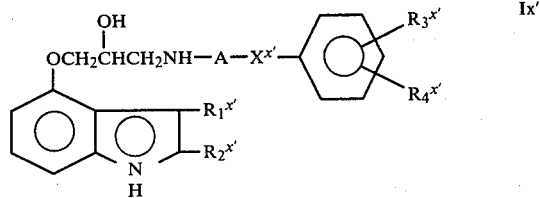

wherein

A is as defined above, $X^{x'}$ is oxygen or sulfur and $R_1^{x'}$ to $R_4^{x'}$ have the significances indicated above for $R_1$ to $R_4$, with the proviso, that $X^{x'}$ is separated by at least 2 carbon atoms from the nitrogen atom of the 3-amino-2-hydroxypropoxy chain.

In accordance with the invention, a compound of formula I may be obtained by a process comprising reacting a corresponding compound of formula II

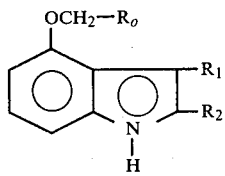

wherein $R_1$ and $R_2$ are as defined above and $R_o$ is a group capable of reacting with an amine to give a 2-amino-1-hydroxyethyl group, with a corresponding compound of formula III $$R—NH_2 \qquad \qquad III$$

wherein R is as defined above.

The present process is an amination by a primary amine. It may be effected in conventional manner for the production of analogous 3-amino-2-hydroxypropoxyaryl compounds. For example $R_o$ may be a group of formula

or a reactive derivative of this group, e.g. of formula —CH(OH)—CH$_2$Y, wherein Y is halogen, preferably chlorine or bromine, or a group $R_y$—SO$_2$—O, wherein $R_y$ is phenyl, tolyl or lower alkyl. Y is especially chlorine. The reaction is effected preferably in an inert organic solvent, e.g. in an appropriate ether such as dioxane. Optionally an excess of a compound of formula III may be used as solvent. Alternatively the reaction may be effected in a fusion melt. Suitable reaction temperatures may be from about 20° to about 200° C., conveniently the reflux temperature of the reaction mixture when a solvent is present.

Free base forms of the compounds of formula I may be converted into salt forms, e.g. into acid addition salt forms, in conventional manner and vice versa. Suitable acids for salt formation include maleic, malonic and fumaric acid. When $R_3$ is hydroxy or $R_c$ is hydrogen, salts may be formed with strong bases, e.g. sodium hydroxide.

In the compounds of formula I, the carbon atom to which the hydroxy group is bound is asymmetrically substituted. The compounds may thus exist in the racemic form or in individual optical isomer form. The preferred optical isomer has the S configuration at the asymmetrically substituted carbon atom of the hydroxypropoxy side chain.

Individual optical isomer forms may be obtained in conventional manner, for example by using optically active starting materials or by fractional crystallisation using optically active acids.

In so far the preparation of any particular starting material is not particularly described, this may be effected in conventional manner. 4-Hydroxyindol-2-carbonitrile and 4-Hydroxy-3-methylindol-2-carbonitrile may be obtained by splitting off of a water molecule from the corresponding 2-carboxamide derivative, e.g. using titanium tetrachloride.

In the following examples all temperatures are in degrees Centigrade and are uncorrected.

EXAMPLE 1

1-(3-Chloro-2-methylindol-4-yloxy)-3-(2-phenoxyethylamino)-2-propanol 5 g 3-chloro-4-(2,3-epoxypropoxy)-2-methylindole, 4.3 g phenoxyethylamine and 75 ml dioxane are heated at 130° for 15 hours in an autoclave. The reaction mixture is allowed to cool down, the excess dioxane is evaporated in a vacuum produced by a waterpump and the excess amine is distilled off under high vacuum at 80°. The reaction mixture is partitioned between aqueous tartaric acid solution and methylene chloride. The aqueous phase is made alkaline with conc. ammonia and extracted with methylene chloride. Evaporation of the organic phase yields the title compound (M.P. of the hydrogen malonate 135°–137° after crystallization from methanol).

From the appropriate compound of formula II, wherein $R_x$ is —CH(OH)—CH$_2$Cl, and the appropriate compound of formula III the following compounds of formula I may be obtained in analogous manner to Example 1:

| Example No. | R | $R_1$ | $R_2$ | M.P. |
|---|---|---|---|---|
| 2 | —C(CH$_3$)$_3$ | H | CN | f 259°–261° |
| 3 | —CH$_2$CH$_2$O—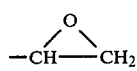 | H | CN | hmi 166°–169° |

-continued

| Example No. | R | $R_1$ | $R_2$ | M.P. |
|---|---|---|---|---|
| 4 | −CH₂CH₂−C₆H₃(OCH₃)(OCH₃) | H | CN | hcl 88° (foam) |
| 5 | −C(CH₃)₂−CH₂−C₆H₄−OH | H | CN | f 172°–175° |
| 6 | −C(CH₃)₂−CH₂−O−C₆H₄−CN | H | CONH₂ | b 198°–200° |
| 7 | −C(CH₃)₂−CH₂−O−C₆H₄−CONH₂ | H | CONH₂ | f 209°–212° |
| 8 | −CH₂CH₂−O−C₆H₅ | H | CONH₂ | hcl 111°–113° |
| 9 | −C(CH₃)₂−CH₂−C₆H₄−OH | H | CONH₂ | f 170°–173° |
| 10 | −CH₂CH₂−C₆H₃(OCH₃)(OCH₃) | H | CONH₂ | hcl 94° (foam) |
| 11 | −C(CH₃)₂−CH₂−C₆H₄−OH | H | CON(H)(CH₃) | f 157°–160° |
| 12 | −C(CH₃)₂−CH₂−C₆H₄−OH | CH₃ | CONH₂ | f 236°–238° |
| 13 | −CH₂CH₂−O−C₆H₅ | H | COOCH(CH₃)₂ | b 121°–124° |
| 14 | −C(CH₃)₂−CH₂−C₆H₄−OH | H | COOCH(CH₃)₂ | b 203°–205° |
| 15 | −C(CH₃)₂−CH₂−C₆H₄−OH | CH₃ | COOCH₂CH₃ | f 241°–243° |
| 16 | −CH₂CH₂−C₆H₃(OCH₃)(OCH₃) | CH₃ | Cl | b 129°–131° |
| 17 | −CH₂CH₂−C₆H₃(OCH₃)(OCH₃) | Cl | CH₃ | hf 99° (sinters) |
| 18 | −CH₂CH₂−C₆H₃(OCH₃)(OCH₃) | CH₃ | Br | b 126°–128° |
| 19 | −C(CH₃)₂−CH₂−C₆H₄−OH | Cl | CH₃ | f 141°–143° |
| 20 | −CH₂CH₂−C₆H₃(OCH₃)(OCH₃) | H | CONHCH₃ | f 121°–124° |
| 21 | −CH₂CH₂−C₆H₃(OCH₃)(OCH₃) | H | CH₂OCH₃ | f 103°–106° |

-continued

| Example No. | R | R₁ | R₂ | M.P. |
|---|---|---|---|---|
| 22 | $-\underset{\underset{CH_3}{\vert}}{\overset{\overset{CH_3}{\vert}}{C}}-CH_2-\text{C}_6\text{H}_4-OH$ | H | CH₂OCH₃ | b 149°–151° | b = free form
f = bis[base]fumarate
hcl = hydrochloride
hf = hydrogen fumarate
hmi = hydrogen maleinate The following compounds of formula I may also be obtained in a manner analogous to Example 1:

| Example No. | R | R₁ | R₂ |
|---|---|---|---|
| 23 | $-\underset{\underset{CH_3}{\vert}}{\overset{\overset{CH_3}{\vert}}{C}}-CH_2-S-\text{C}_6\text{H}_4-OCH(CH_3)_2$ | Br | H |
| 24 | $-\underset{\underset{CH_3}{\vert}}{CH}-(CH_2)_3-S-\text{C}_6\text{H}_3(Cl)-Cl$ | CH₃ | COOH |
| 25 | $-CH\overset{CH_2CH_3}{\underset{(CH_2)_3CH_3}{\diagup\diagdown}}$ | CH₃ | CN |
| 26 | $-\underset{\underset{CH_3}{\vert}}{\overset{\overset{CH_3}{\vert}}{C}}-(CH_2)_2-\text{C}_6\text{H}_4-NHCOCH(CH_3)_2$ | CH₃ | CH₂OH |
| 27 | $-(CH_2)_2-S-\text{C}_6\text{H}_3(F)-Br$ | H | $CON\overset{CH_3}{\underset{CH(CH_3)_2}{\diagup\diagdown}}$ |

The compounds of formula I are useful because they exhibit pharmacological activity in animals.

The compounds of formula I possess cardiovascular adrenergic α- and β-blocking activity.

In particular, they inhibit α-adrenoceptors in isolated spiral strips of the Vena femoralis of dogs (E. Müller-Schweinitzer and E. Stürmer, Br. J. Pharmacol. [1974] 51, 441–446) and inhibit β-adrenoceptors in isolated spiral strips of the Arteria coronaria of dogs (T. J. Bücher et al., Naunyn-Schmiedeberg's Arch. Pharmacol. 280 [1973] 153–160). These actions take place at a bath concentration of from about $10^{-9}$ to about $10^{-6}$ M. In the spontaneously beating guinea pig atrium (K. Saameli, Helv. Physiol. Acta 25 [1967] CR 219–CR 221) they inhibit the positive inotropic adrenaline effect at bath concentrations of from 0.005 to 2.5 mg/l.

The compounds are therefore useful as α- and β-blocking agents, e.g. for the therapy and possibly prophylaxis of diseases related to an adrenergic vasoconstriction, and of coronary diseases, especially of Angina pectoris. They are also useful for the treatment of diseases related to an inhibition of bowel motility, especially of paralytic ileus. In view of their antiarrhythmic activity they are also useful as antiarrhythmics.

The compounds of Example 1 to 19 exhibit particularly interesting activity as α- and β-blocker. The Example 10 compound exhibits particularly interesting activity as a β-blocker.

For these uses the dosage will, of course, vary depending on the compound employed, mode of administration and treatment desired. However, in general, satisfactory results are obtained when administered at a daily dosage of from about 0.01 mg to about 3 mg per kg animal body weight, conveniently given in divided doses 2 to 4 times a day or in sustained release form. For the larger mammals, the total daily dosage is in the range from about 20 to about 100 mg, and dosage forms suitable for oral administration comprise from about 5 mg to about 50 mg of the compounds admixed with a solid or liquid pharmaceutical carrier or diluent.

The compounds of formula I also exhibit antihypertensive activity.

This is indicated in standard tests, e.g. in the Grollman rat test [A. Grollman, Proc. Soc. Exp. Biol. and Med. 57 (1944) 102] on s.c. administration of from 0.1 to 10 mg/kg animal body weight of the compounds, and on p.o. administration of from 10 to 100 mg/kg.

The compounds are therefore useful as antihypertensive agents. Especially interesting in this indication is the compound of Example 1.

For this use the dosage will, of course, vary depending on the compound employed, mode of administration and treatment desired. However, in general, satisfactory results are obtained when administered at a daily dosage of from about 0.1 mg to about 10 mg per kg animal body weight, conveniently given in divided doses 2 to 4 times a day or in sustained release form. For the larger mammals, the total daily dosage is in the range from about 1 to about 50 mg, and dosage forms suitable for oral administration comprise from about 0.25 mg to about 25 mg of the compounds admixed with a solid or liquid pharmaceutical carrier or diluent.

The compounds of formula I also possess interesting metabolic activity.

In particular, they inhibit glycerol release and hyperglycemia stimulated by isoproterenol in standard tests.

Inhibition of glycerol release is e.g. indicated as follows:

(i) In vitro

Isolated fat cells are obtained from dog subcutaneous tissue, and from rat and guinea pig epididymal fat pads, in accordance with the method of M. Rodbell [*J. Biol. Chem.* 239, 375–380 (1964)]. Cells from one of the animals are dispersed in Krebs phosphate buffer containing 4% bovine serum albumin. 1 ml aliquots of the cell suspension in plastic incubation flasks are treated with the test substance at from about 0.1 to about 10 mg/liter and isoproterenol at $10^{-7}$ Molar. The glycerol release is determined in conventional manner, e.g. according to the method of S. Laurell et al, Helv. Chim. Acta 13, 317–322 (1966).

(ii) In vivo

Rats are fasted for 16 hours. A sub-cutaneous injection of 400 μg/kg of isoproterenol results in a glycerol concentration in the blood plasma of 400% the original value. This increased glycerol concentration remains constant for ca. 60 minutes and acts as a control value. The test substance is administered s.c. at a dose of from about 0.1 to about 10 mg/kg body weight 10 minutes before the isoproterenol injection, and the animals are decapitated 40 minutes after the isoproterenol injection. The glycerol concentration in the blood is calculated in conventional manner, e.g. using the conventional glycero-3-phosphate-dehydrogenase method [according S. Laurell et al; reference as mentioned above].

Inhibition of hyperglycemia is e.g. indicated as follows:

In the above-mentioned rat in vivo test the glucose concentration in the blood is determined in conventional manner, e.g. using the ferricyanide method. In the control animals the glucose concentration doubles after 40 minutes after isoproterenol administration. The compounds are administered s.c. at a dose of from about 0.1 to about 10 mg/kg animal body weight.

The compounds are therefore useful in the treatment of lipolysis in the blood and hyperglycemia induced by emotional stress, and are useful therefore for the treatment of, or prophylaxis of myocardial infarction and appetite induced by emotional stress.

Especially interesting in this indication are the compounds of Examples 2, 5 and 19, especially the compound of Example 5.

For these indications as metabolic inhibitors the dosage will, of course, vary depending on the compound employed, mode of administration and treatment desired. However, in general, satisfactory results are obtained when administered at a daily dosage of from about 0.01 mg to about 5 mg per kg animal body weight, conveniently given in divided doses 2 to 4 times a day or in sustained release form. For the larger mammals, the total daily dosage is in the range from about 0.1 to about 200 mg, and dosage forms suitable for oral administration comprise from about 0.025 mg to about 100 mg of the compounds admixed with a solid or liquid pharmaceutical carrier or diluent.

One group of compounds of formula I, i.e. the compounds of formula Iu

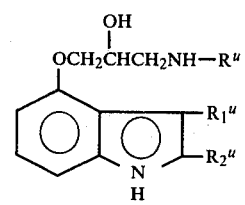

wherein
$R^u$ is a group

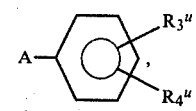

wherein A is as defined above,
$R_1^u$, $R_2^u$ and $R_4^u$ have the significances indicated above for $R_1$, $R_2$ and $R_4$ and
$R_3^u$ with the exception of hydrogen has the significance indicated above for $R_3$,
with the provisos, that (a) the phenyl ring is separated by at least two carbon atoms from the nitrogen atom of the 3-amino-2-hydroxypropoxy chain and (b) when $R_2^u$ is cyano, $R_1^u$ additionally may be alkyl of 3 to 7 carbon atoms, exhibit activities that are unexpectedly more interesting than those exhibited by known compounds of similar structure.

A preferred group of compounds of formula Iu are the compounds of formula Iu'

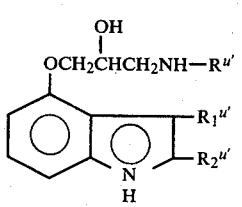

wherein
$R^{u'}$ is a group

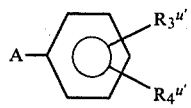

wherein A is as defined above,
$R_3^{u'}$ is alkoxy of 1 to 4 carbon atoms or halogen of atomic number of from 9 to 35,
$R_4^{u'}$ is hydrogen and, when $R_3^{u'}$ is alkoxy of 1 to 4 carbon atoms, $R_4^{u'}$ additionally may be alkoxy of 1 to 4 carbon atoms or, when $R_3^{u'}$ is halogen of atomic number of from 9 to 35, $R_4^{u'}$ additionally may be halogen of atomic number of from 9 to 35,
either (i) $R_1^{u'}$ is hydrogen or methyl and
$R_2^{u'}$ is cyano, $COOR_c$ or $CH_2OR_3$, wherein $R_c$ and $R_e$ are as defined above,
or (ii) either $R_1^{u'}$ is methyl and $R_2^{u'}$ is halogen of atomic number of from 17 to 35 or $R_1^{u'}$ is halogen of atomic number of from 17 to 35 and $R_2^{u'}$ is hydrogen or methyl, with the provisos, that (a) the phenyl ring is separated by at least 2 carbon atoms from the nitrogen atom of the 3-amino-2-hydroxypropoxy chain and (b) when $R_2^{u'}$ is cyano, $R_1^{u'}$ additionally may be alkyl of 3 to 7 carbon atoms.

In general, the 2(S) optical isomers are more active than the 2(R) optical isomers in the cardiovascular β-blocking, metabolic and blood pressure lowering tests.

The compounds of formula I may be administered in pharmaceutically acceptable salt form. Such salt forms exhibit the same order of activity as the free forms and are readily prepared in conventional manner. The present invention also provides a pharmaceutical composition comprising a compound of formula I, in free form or in pharmaceutically acceptable salt form, in association with a pharmaceutical carrier or diluent. Such compositions may be in the form of, for example, a solution or a tablet.

Further groups of compounds of formula I are the following:

(a) Compounds of formula Ipa

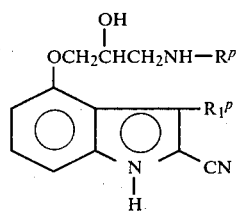

wherein
$R^p$ is alkyl of 3 to 7 carbon atoms and
$R_1^p$ is hydrogen or methyl;

(b) compounds of formula Ipb

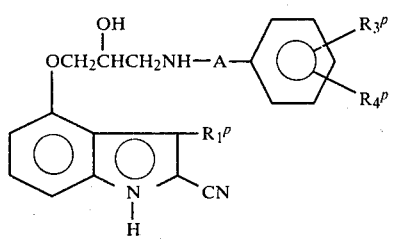

wherein
$R_1^p$ and A are as defined above
$R_3^p$ is hydroxy, alkoxy of 1 to 4 carbon atoms, halogen of atomic number of from 9 to 35, cyano, carbamoyl or acetamido and
$R_4^p$ is hydrogen and, when $R_3^p$ is alkoxy of 1 to 4 carbon atoms, $R_4^p$ additionally may be alkoxy of 1 to 4 carbon atoms, or when $R_3^p$ is halogen of atomic number of from 9 to 35, $R_4^p$ additionally may be halogen of atomic number of from 9 to 35,
with the proviso that the phenyl ring is separated by at least 2 carbon atoms from the nitrogen atom of the 3-amino-2-hydroxypropoxy moiety;

(c) compounds of formula Ipc

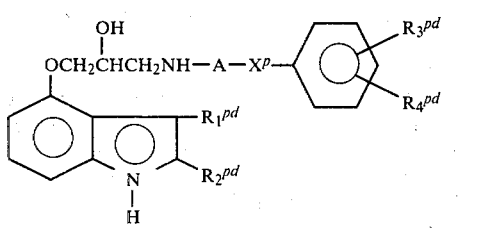

wherein
A, $R_1^p$, $R_3^p$, $R_4^p$, $R_a$ and $R_b$ are as defined above, with the proviso that the phenyl ring is separated by at least 2 carbon atoms from the nitrogen atom of the 3-amino-2-hydroxypropoxy moiety;

(d) compounds of formula Ipd

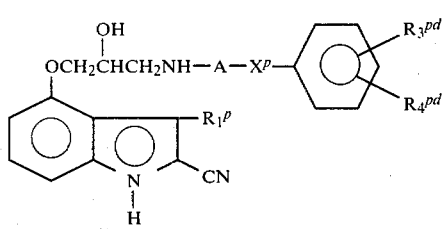

wherein
A is as defined above,
either (i) $R_1^{pd}$ is halogen of atomic number of from 17 to 35 and $R_2^{pd}$ is hydrogen or methyl
or (ii) $R_1^{pd}$ is methyl and $R_2^{pd}$ is halogen of atomic number of from 17 to 35,
$R_3^{pd}$ is hydrogen or has the significances indicated above for $R_3^p$
$R_4^{pd}$ has the significances indicated above for $R_4^p$ and
$X^p$ is oxygen or sulfur,
with the proviso that $X^p$ is separated by at least 2 carbon atoms from the nitrogen atom of the 3-amino-2-hydroxypropoxy moiety;

(e) compounds of formula Ipe

OH
|
OCH₂CHCH₂NH—A—X$^p$—⟨ring⟩—$R_3^{pd}$, $R_4^{pd}$
Ipe
with $R_1^p$, CN on indole wherein
A, $X^p$, $R_1^p$, $R_3^{pd}$ and $R_4^{pd}$ are as defined above, with the proviso that the phenyl ring is separated by at least 2 carbon atoms for the nitrogen atom of the 3-amino-2-hydroxypropoxy moiety;

(f) compounds of formula Ipf

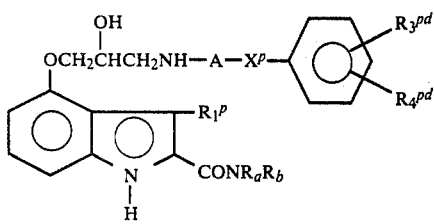

wherein

A, $X^p$, $R_1^p$, $R_3^{pd}$, $R_4^{pd}$, $R_a$ and $R_b$ are as defined above, with the proviso that the phenyl ring is separated by at least 2 carbon atoms from the nitrogen atom of the 3-amino-2-hydroxypropoxy moiety;

(g) compounds of formula Ipg

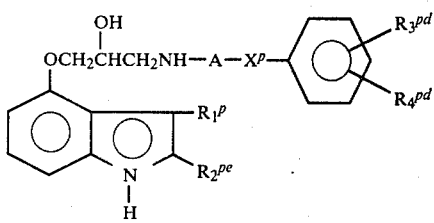

wherein

A, $X^p$, $R_1^p$, $R_3^{pd}$ and $R_4^{pd}$ are as defined above and $R_2^{pe}$ is $CH_2OH$ or $COOR_c$, wherein $R_c$ is as defined above, with the proviso, that the phenyl ring is separated by at least 2 carbon atoms from the nitrogen atom of the 3-amino-2-hydroxypropoxy moiety;

(h) compounds of formula Iph

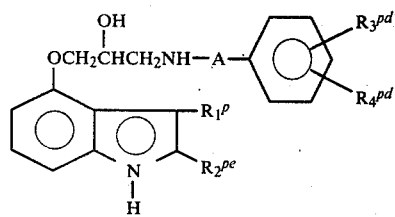

wherein A, $R_1^p$, $R_2^{pe}$, $R_3^{pd}$ and $R_4^{pd}$ are as defined above, with the proviso, that the phenyl ring is separated by at least 2 carbon atoms from the nitrogen atom of the 3-amino-2-hydroxypropoxy moiety;

(i) compounds of formula Ipi

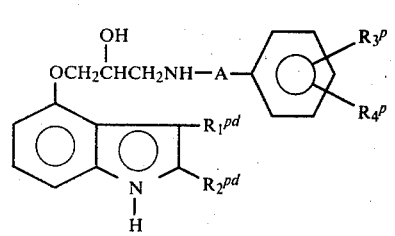

wherein A, $R_1^{pd}$, $R_2^{pd}$, $R_3^p$ and $R_4^p$ are as defined above, with the proviso, that the phenyl ring is separated by at least 2 carbon atoms from the nitrogen atom of the 3-amino-2-hydroxypropoxy moiety.

In a 1st group of compounds X is a bond.
In a 2nd group of compounds X is oxygen.
In a 3rd group of compounds X is sulfur.
In a 4th group of compounds $R_3$ is other than $NHCOR_d$.
In a 5th group of compounds $R_3$ is $NHCOR_d$.
In a 6th group of compounds $R_2$ is cyano.
In a 7th group of compounds $R_2$ is $CONR_aR_b$.
In a 8th group of compounds $R_2$ is $COOR_c$.
In a 9th group of compounds $R_2$ is $CH_2OR_e$.
In a 10th group of compounds $R_2$ is halogen.
In a 11th group of compounds $R_2$ is hydrogen.
In a 12th group of compounds $R_2$ is methyl.
In a 13th group of compounds R is alkyl.

I claim:

1. A compound of formula I

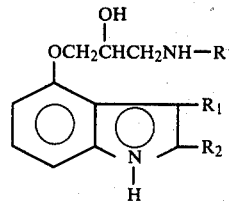

wherein
R is a group

A—X—[phenyl with $R_3$, $R_4$]

wherein
A is alkylene of 2 to 5 carbon atoms,
X is a bond, oxygen or sulfur,
$R_3$ is hydrogen, hydroxy, alkoxy of 1 to 4 carbon atoms, halogen of atomic member of from 9 to 35, cyano, carbamoyl or a group $NHCOR_d$, wherein $R_d$ is alkyl of 1 to 4 carbon atoms, and
$R_4$ is hydrogen and, when $R_3$ is alkoxy of 1 to 4 carbon atoms, $R_4$ additionally may be alkoxy of 1 to 4 carbon atoms or, when $R_3$ is halogen of atomic number of from 9 to 35, $R_4$ additionally may be halogen of atomic number of from 9 to 35
either
(i) $R_1$ is hydrogen or methyl and
$R_2$ is cyano, $CONR_aR_b$, $COOR_c$ or $CH_2OR_e$, wherein $R_a$, $R_b$, $R_c$ and $R_e$ independently are hydrogen or alkyl of 1 to 4 carbon atoms,
or
(ii) either $R_1$ is methyl and $R_2$ is halogen of atomic number of from 17 to 35
or
$R_1$ is halogen of atomic number of from 17 to 35 and $R_2$ is hydrogen or methyl,
with the provisos that
(a) X is separated from the nitrogen atom of the 3-amino-2-hydroxypropoxy chain by at least 2 carbon atoms,
(b) when X is a bond, $R_3$ is other than hydrogen and
(c) when $R_2$ is cyano, R additionally may be alkyl of 3 to 7 carbon atoms,
in free form or in pharmaceutically acceptable salt form.

2. A pharmaceutical composition useful in treating vasoconstriction, arrhythmia, hypertension, and myocardial infarction comprising a therapeutically effective amount of a compound of claim 1, in association with a pharmaceutical carrier or diluent.

3. A method of treating diseases related to an adrenergic vasoconstriction, or coronary diseases, or diseases related to an inhibition of bowel motility, or arrhythmies, or hypertension, or lipolysis in the blood, hyperglycemia, appetite or myocardial infarction induced by emotional stress, which comprises administering to an animal in need of such treatment a therapeutically effective amount of a compound of claim 1.

4. A compound of claim 1 of formula Ix

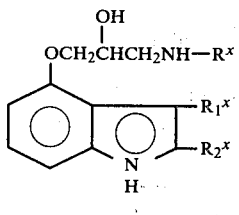

wherein
$R^x$ is a group

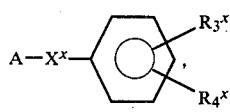

wherein A is as defined above,
either
(i) $X^x$ is oxygen or sulfur and $R_1^x$ to $R_4^x$ have the significances indicated above for $R_1$ to $R_4$
or
(ii) $X^x$ is a bond and
either
(j) $R_3^x$ is alkoxy of 1 to 4 carbon atoms or halogen of atomic number of from 9 to 35,
$R_4^x$ is hydrogen and, when $R_3^x$ is alkoxy of 1 to 4 carbon atoms, $R_3^x$ additionally may be alkoxy of 1 to 4 carbon atoms or, when $R_3^x$ is halogen of atomic number of from 9 to 35, $R_4^x$ additionally may be halogen of atomic number of from 9 to 35,
$R_1^x$ is hydrogen or methyl and
$R_2^x$ is $CONR_aR_b$, wherein $R_a$ and $R_b$ are as defined above,
or
(jj) $R_3^x$ is hydroxy, cyano, carbamoyl or $NHCOR_d$, wherein $R_d$ is as defined above,
$R_4^x$ is hydrogen and
$R_1^x$ and $R_2^x$ have the significances indicated above for $R_1$ and $R_2$,
with the proviso, that $X^x$ is separated by at least 2 carbon atoms from the nitrogen atom of the 3-amino-2-hydroxypropoxy chain.

5. A compound of claim 1 of formula Ix'

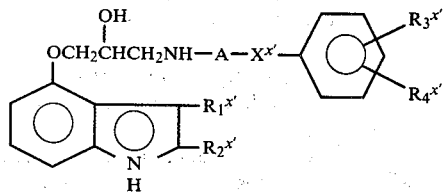

wherein

A is as defined above,
$X^{x'}$ is oxygen or sulfur and
$R_1^{x'}$ to $R_4^{x'}$ have the significances indicated above for $R_1$ to $R_4$,
with the proviso, that $X^{x'}$ is separated by at least 2 carbon atoms from the nitrogen atom of the 3-amino-2-hydroxypropoxy chain.

6. A compound of claim 1 of formula Iu,

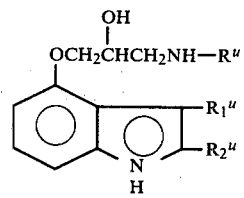

wherein
$R^u$ is a group

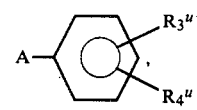

wherein
A is as defined above,
$R_1^u$, $R_2^u$ and $R_4^u$ have the significances indicated above for $R_1$, $R_2$ and $R_4$ and
$R_3^u$ with the exception of hydrogen has the significances indicated above for $R_3$,
with the provisos, that
(a) the phenyl ring is separated by at least two carbon atoms from the nitrogen atom of the 3-amino-2-hydroxypropoxy chain and
(b) when $R_2^u$ is cyano, $R_1^u$ additionally may be alkyl of 3 to 7 carbon atoms, 7. A compound of claim 1 of formula Iu',

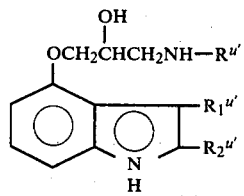

wherein
$R^{u'}$ is a group

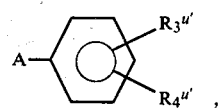

wherein A is as defined above,
$R_3^{u'}$ of 1 to 4 carbon atoms or halogen of atomic number of from 9 to 35,
$R_4^{u'}$ is hydrogen and, when $R_3^{u'}$ is alkoxy of 1 to 4 carbon atoms, $R_4^{u'}$ additionally may be alkoxy of 1 to 4 carbon atoms or, when $R_3^{u'}$ is halogen of atomic number of from 9 to 35, $R_4^{u'}$ additionally may be halogen of atomic number of from 9 to 35,
either (i) $R_1{}^{u'}$ is hydrogen or methyl and $R_2{}^{u'}$ is cyano, COOR$_c$ or CH$_2$OR$_e$, wherein R$_c$ and R$_e$ are as defined above, or (ii) either $R_1{}^{u'}$ is methyl and $R_2{}^{u'}$ is halogen of atomic number of from 17 to 35 or $R_1{}^{u'}$ is halogen of atomic number of from 17 to 35 and $R_2{}^{u'}$ is hydrogen or methyl, with the provisos, that (a) the phenyl ring is separated by at least 2 carbon atoms from the nitrogen atom of the 3-amino-2-hydroxypropoxy chain and (b) when $R_2{}^{u'}$ is cyano, $R_1{}^{u'}$ additionally may be alkyl of 3 to 7 carbon atoms.

8. A compound according to claim 1 which is 1-(3-chloro-2-methylindol-4-yloxy)-3-(2-phenoxyethylamino)-2-propanol, or a pharmaceutically acceptable acid addition salt thereof.

9. A compound of claim 1 wherein R is —C(CH$_3$)$_3$, R$_1$ is H and R$_2$ is CN, or a pharmaceutically acceptable acid addition salt thereof.

10. A compound of claim 1 wherein R is

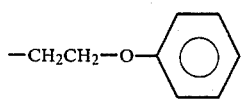

R$_1$ is H, and R$_2$ is CN, or a pharmaceutically acceptable acid addition salt thereof.

11. A compound of claim 1 wherein R is

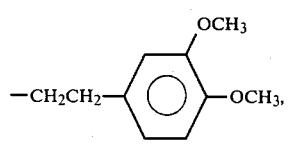

R$_1$ is H, and R$_2$ is CN, or a pharmaceutically acceptable acid addition salt thereof.

12. A compound of claim 1 wherein R is

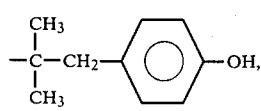

R$_1$ is H, and R$_2$ is CN, or a pharmaceutically acceptable acid addition salt thereof.

13. A compound of claim 1 wherein R is

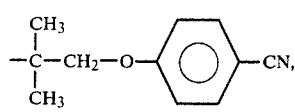

R$_1$ is H, and R$_2$ is CONH$_2$, or a pharmaceutically acceptable acid addition salt thereof.

14. A compound of claim 1 wherein R is

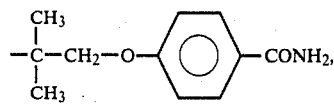

R$_1$ is H, and R$_2$ is CONH$_2$, or a pharmaceutically acceptable acid addition salt thereof.

15. A compound of claim 1 wherein R is

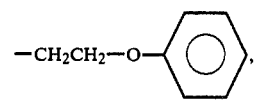

R$_1$ is H, and R$_2$ is CONH$_2$, or a pharmaceutically acceptable acid addition salt thereof.

16. A compound of claim 1 wherein R is

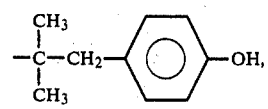

R$_1$ is H, and R$_2$ is CONH$_2$, or a pharmaceutically acceptable acid addition salt thereof.

17. A compound of claim 1 wherein R is

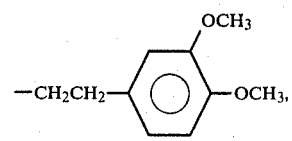

R$_1$ is H, and R$_2$ is CONH$_2$, or a pharmaceutically acceptable acid addition salt thereof.

18. A compound of claim 1 wherein R is

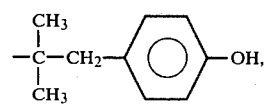

R$_1$ is H, and R$_2$ is

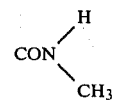

or a pharmaceutically acceptable acid addition salt thereof.

19. A compound of claim 1 wherein R is

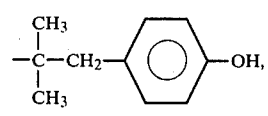

R$_1$ is CH$_3$, and R$_2$ is CONH$_2$, or a pharmaceutically acceptable acid addition salt thereof.

20. A compound of claim 1 wherein R is

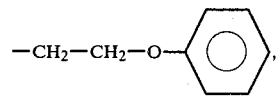

$R_1$ is H, and $R_2$ is COOCH(CH$_3$)$_2$, or a pharmaceutically acceptable acid addition salt thereof.

21. A compound of claim 1 wherein R is

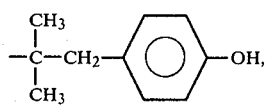

$R_1$ is H, and $R_2$ is COOCH(CH$_3$)$_2$, or a pharmaceutically acceptable acid addition salt thereof.

22. A compound of claim 1 wherein R is

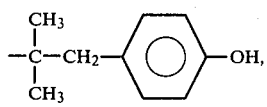

$R_1$ is CH$_3$, and $R_2$ is COOCH$_2$CH$_3$, or a pharmaceutically acceptable acid addition salt thereof.

23. A compound of claim 1 wherein R is

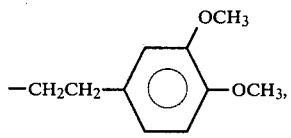

$R_1$ is CH$_3$, and $R_2$ is Cl, or a pharmaceutically acceptable acid addition salt thereof.

24. A compound of claim 1 wherein R is

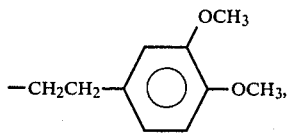

$R_1$ is Cl, and $R_2$ is CH$_3$, or a pharmaceutically acceptable acid addition salt thereof.

25. A compound of claim 1 wherein R is

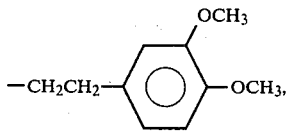

$R_1$ is CH$_3$, and $R_2$ is Br, or a pharmaceutically acceptable acid addition salt thereof.

26. A compound of claim 1 wherein R is

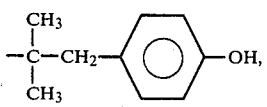

$R_1$ is Cl, and $R_2$ is CH$_3$, or a pharmaceutically acceptable acid addition salt thereof.

27. A compound of claim 1 wherein R is

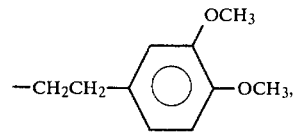

$R_1$ is H, and $R_2$ is CONHCH$_3$, or a pharmaceutically acceptable acid addition salt thereof.

28. A compound of claim 1 wherein R is

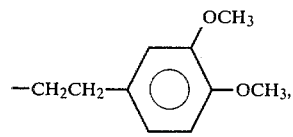

$R_1$ is H, and $R_2$ is CH$_2$OCH$_3$, or a pharmaceutically acceptable acid addition salt thereof.

29. A compound of claim 1 wherein R is

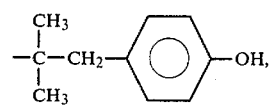

$R_1$ is H, and $R_2$ is CH$_2$OCH$_3$, or a pharmaceutically acceptable acid addition salt thereof.

30. A compound of the formula

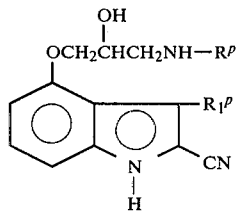

wherein
$R^p$ is alkyl of 3 to 7 carbon atoms, and
$R_1^p$ is hydrogen or methyl,
or a pharmaceutically acceptable acid addition salt thereof.

31. A compound of the formula

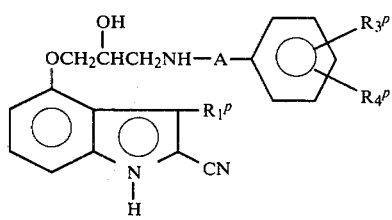

wherein
$R_1^p$ is as defined in claim 30,
A is alkylene of 2 to 5 carbon atoms,
$R_3^p$ is hydroxy, alkoxy of 1 to 4 carbon atoms, halogen of atomic number from 9 to 35, cyano, carbamoyl or acetamido, and $R_4^p$ is hydrogen and, when $R_3^p$ is alkoxy of 1 to 4 carbon atoms, $R_4^p$ additionally may be alkoxy of 1 to 4 carbon atoms, or when $R_3^p$ is halogen of atomic number of from 9 to 35, $R_4^p$ additionally may be halogen of atomic number of from 9 to 35, with the proviso that the phenyl ring is separated by at least 2 carbon atoms from the nitrogen atom of the 3-amino-2-hydroxypropoxy moiety, or a pharmaceutically acceptable acid addition salt thereof.

32. A compound of the formula

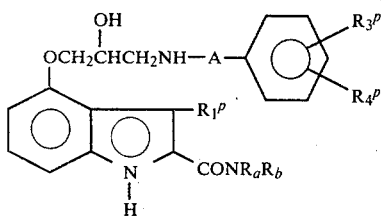

wherein

A, $R_1^p$, $R_3^p$ and $R_4^p$ are as defined in claim 10, and $R_a$ and $R_b$ are, independently, hydrogen or alkyl of 1 to 4 carbon atoms, with the proviso that the phenyl ring is separated by at least 2 carbon atoms from the nitrogen atom of the 3-amino-2-hydroxypropoxy moiety, or a pharmaceutically acceptable acid addition salt thereof.

33. A compound of the formula

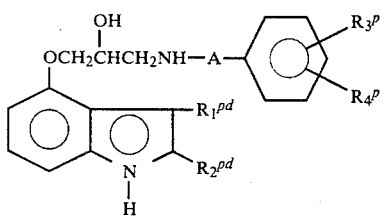

wherein

A, $R_1^{pd}$ and $R_2^{pd}$ are as defined in claim 34, $R_3^p$ is hydroxy, alkoxy of 1 to 4 carbon atoms, halogen of atomic number of from 9 to 35, cyano, carbamoyl or acetamido, and $R_4^p$ is hydrogen and, when $R_3^p$ is alkoxy of 1 to 4 carbon atoms, $R_4^p$ additionally may be alkoxy of 1 to 4 carbon atoms, or when $R_3^p$ is halogen of atomic number of from 9 to 35, $R_4^p$ additionally may be halogen of atomic number of from 9 to 35, with the proviso that the phenyl ring is separated by at least 2 carbon atoms from the nitrogen atom of the 3-amino-2-hydroxypropoxy moiety, or a pharmaceutically acceptable acid addition salt thereof.

34. A compound of the formula

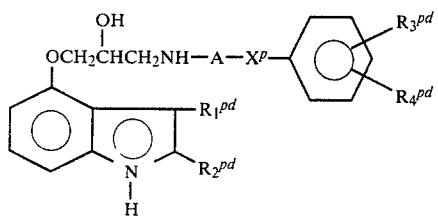

wherein

A is as defined in claim 31, either (i) $R_1^{pd}$ is halogen of atomic number of from 17 to 35 and $R_2^{pd}$ is hydrogen or methyl or (ii) $R_1^{pd}$ is methyl and $R_2^{pd}$ is halogen of atomic number of from 17 to 35, $R_3^{pd}$ is hydrogen or has the significance defined above for $R_3^p$ in claim 31, $R_4^{pd}$ is as defined in claim 31 for $R_4^p$, and $X^p$ is oxygen or sulfur, with the proviso that $X^p$ is separated by at least 2 carbon atoms from the nitrogen atom of the 3-amino-2-hydroxypropoxy moiety, or a pharmaceutically acceptable acid addition salt thereof.

35. A compound of the formula

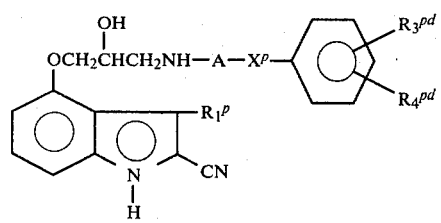

wherein

A is alkylene of 2 to 5 carbon atoms, $X^p$ is oxygen or sulfur, $R_1^p$ is hydrogen or methyl, and $R_3^{pd}$ and $R_4^{pd}$ are as defined in claim 34, with the proviso that the phenyl ring is separated by at least 2 carbon atoms from the nitrogen atom of the 3-amino-2-hydroxypropoxy moiety, or a pharmaceutically acceptable acid addition salt thereof.

36. A compound of the formula

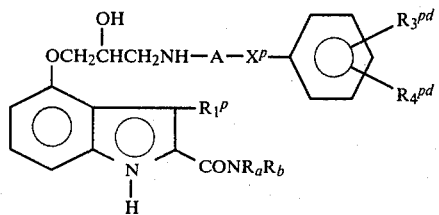

wherein

A, $X^p$, $R_1^p$, $R_3^{pd}$ and $R_4^{pd}$ are as defined in claim 35, and $R_a$ and $R_b$ are, independently, hydrogen or alkyl of 1 to 4 carbon atoms, with the proviso that the phenyl ring is separated by at least 2 carbon atoms from the nitrogen atom of the 3-amino-2-hydroxypropoxy moiety, or a pharmaceutically acceptable acid addition salt thereof.

37. A compound of the formula

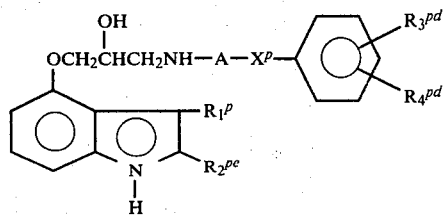

wherein

A, $X^p$, $R_1^p$, $R_3^{pd}$ and $R_4^{pd}$ are as defined in claim 35, and $R_2^{pe}$ is $CH_2OH$ or $COOR_c$ wherein $R_c$ is hydrogen or alkyl of 1 to 4 carbon atoms, with the proviso that the phenyl ring is separated by at least 2 carbon atoms from the nitrogen atom of the 3-amino-2-hydroxypropoxy moiety, or a pharmaceutically acceptable acid addition salt thereof.

38. A compound of the formula

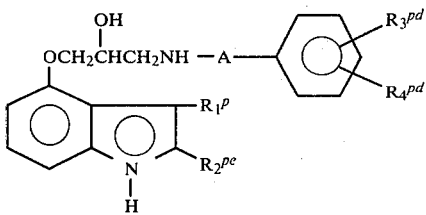

wherein A, $R_1^p$, $R_2^{pe}$, $R_3^{pd}$ and $R_4^{pd}$ are as defined in claim 37, with the proviso that the phenyl ring is separated by at least 2 carbon atoms from the nitrogen atom of the 3-amino-2-hydroxypropoxy moiety, or a pharmaceutically acceptable acid addition salt thereof.

* * * * *

UNITED STATES PATENT AND TRADEMARK OFFICE
CERTIFICATE OF CORRECTION

PATENT NO. : 4,235,919

DATED : Nov. 25, 1980

INVENTOR(S) : RICHARD BERTHOLD

It is certified that error appears in the above—identified patent and that said Letters Patent is hereby corrected as shown below:

Col. 7, line 65, delete "to" and insert in its place -- and --.

Col. 10, line 66, change "$CH_2OR_3$" to -- $CH_2OR_e$ --.

Col. 15, line 41, change "$R_3^x$" to -- $R_4^x$ --.

Col. 16, line 61, after "$R_3^{u'}$", please insert -- is alkoxy --.

Signed and Sealed this

Twenty-seventh Day of July 1982

[SEAL]

Attest:

*Attesting Officer*

GERALD J. MOSSINGHOFF

*Commissioner of Patents and Trademarks*